(12) United States Patent
Schanz

(10) Patent No.: US 10,610,213 B2
(45) Date of Patent: Apr. 7, 2020

(54) FIXATION UNIT AND HANDLING DEVICE FOR A SUTURE-LESS FIXATION OF TISSUE

(71) Applicant: KARL STORZ GmbH & Co. KG, Tuttlingen (DE)

(72) Inventor: Steffen Schanz, Rottweil (DE)

(73) Assignee: KARL STORZ SE & Co. KG, Tuttlingen (DE)

( * ) Notice: Subject to any disclaimer, the term of this patent is extended or adjusted under 35 U.S.C. 154(b) by 217 days.

(21) Appl. No.: 15/661,139

(22) Filed: Jul. 27, 2017

(65) Prior Publication Data

US 2018/0028170 A1 Feb. 1, 2018

(30) Foreign Application Priority Data

Jul. 27, 2016 (DE) .................. 10 2016 113 797

(51) Int. Cl.
*A61B 17/04* (2006.01)
*A61F 2/08* (2006.01)

(52) U.S. Cl.
CPC ........ *A61B 17/0401* (2013.01); *A61F 2/0811* (2013.01); *A61B 2017/0403* (2013.01); *A61B 2017/0409* (2013.01); *A61B 2017/0412* (2013.01); *A61B 2017/0445* (2013.01); *A61F 2002/0829* (2013.01); *A61F 2002/0864* (2013.01); *A61F 2002/0888* (2013.01)

(58) Field of Classification Search
CPC ............ A61B 17/0401; A61B 17/0642; A61B 2017/0409; A61B 2017/0403; A61B 2017/0412; A61B 2017/0445; A61B 17/688; A61F 2/0811; A61F 2002/0829; A61F 2002/0864; A61F 2002/0888
See application file for complete search history.

(56) References Cited

U.S. PATENT DOCUMENTS

| | | | |
|---|---|---|---|
| 5,013,316 A | 5/1991 | Goble et al. | |
| 5,167,664 A * | 12/1992 | Hodorek | A61B 17/8685 606/306 |
| 5,584,835 A | 12/1996 | Greenfield | |
| 6,056,751 A | 5/2000 | Fenton, Jr. | |
| 6,162,234 A | 12/2000 | Freedland et al. | |
| 6,235,058 B1 * | 5/2001 | Huene | A61F 2/08 606/151 |
| 6,863,072 B1 * | 3/2005 | Sinnott | A61F 2/0805 128/892 |

(Continued)

FOREIGN PATENT DOCUMENTS

| | | |
|---|---|---|
| DE | 299 22 088 U1 | 5/2000 |
| DE | 10 2006 010 116 A1 | 8/2007 |

(Continued)

*Primary Examiner* — Tuan V Nguyen
(74) *Attorney, Agent, or Firm* — Muncy, Geissler, Olds & Lowe, P.C.

(57) ABSTRACT

A fixation unit for a suture-less fixation of tissue at a bone comprises an anchor element that is arranged to be fixed to a bone, and a retaining element that is arranged to be coupled with the anchor element to attach a tissue section to the bone. The anchor element and the retaining element are lockable to one another and form therebetween a retaining zone into which the tissue section is mountable. A handling device comprises a mounting tool that is arranged for inserting the fixation unit.

13 Claims, 8 Drawing Sheets

(56) References Cited

U.S. PATENT DOCUMENTS

| | | | |
|---|---|---|---|
| 7,074,203 B1 * | 7/2006 | Johanson | A61F 2/0805 |
| | | | 411/34 |
| 2002/0120274 A1 | 8/2002 | Overaker et al. | |
| 2003/0229349 A1 * | 12/2003 | Wellisz | A61B 17/688 |
| | | | 606/70 |
| 2007/0167950 A1 | 7/2007 | Tauro et al. | |
| 2007/0203498 A1 | 8/2007 | Gerber et al. | |
| 2012/0004675 A1 | 1/2012 | Jiang et al. | |

FOREIGN PATENT DOCUMENTS

| | | |
|---|---|---|
| DE | 602 17 981 T2 | 11/2007 |
| WO | WO 01/80751 A1 | 11/2001 |

* cited by examiner

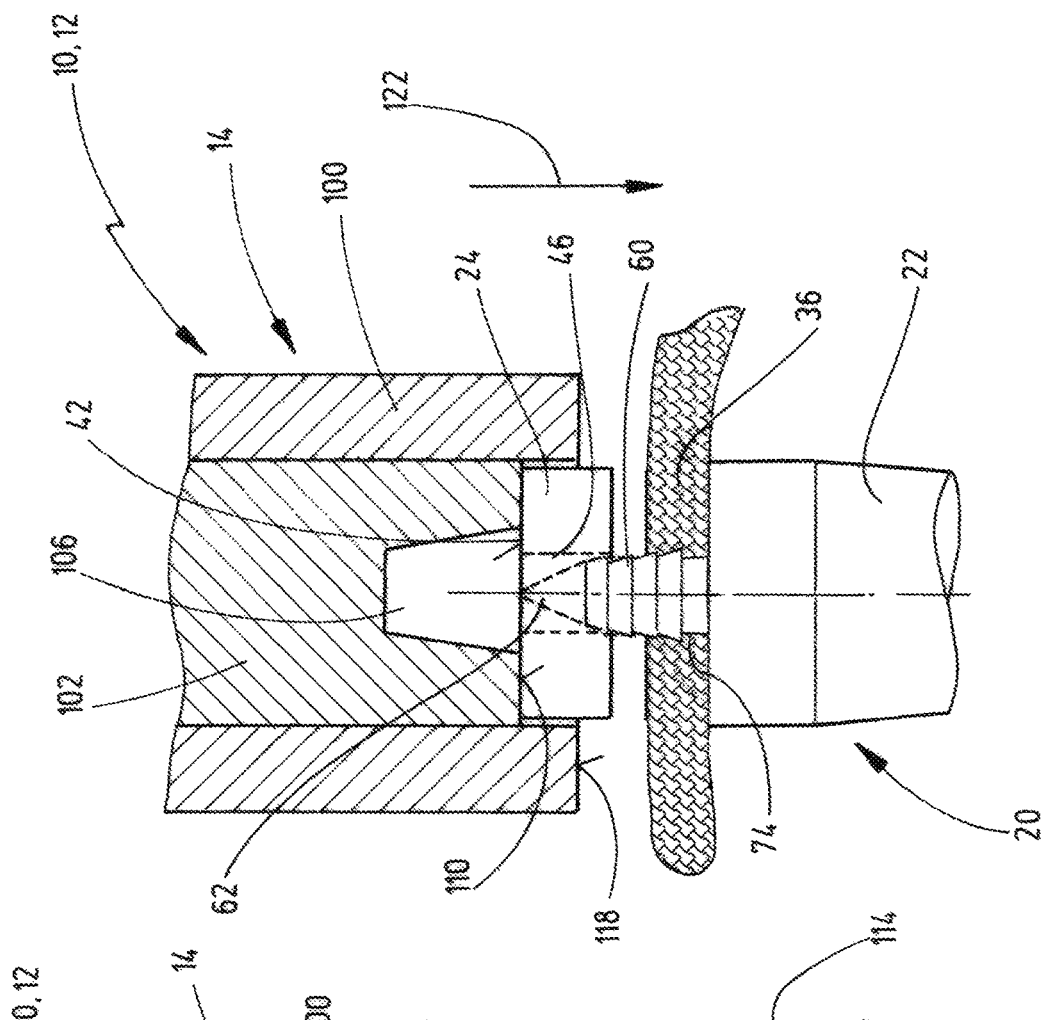
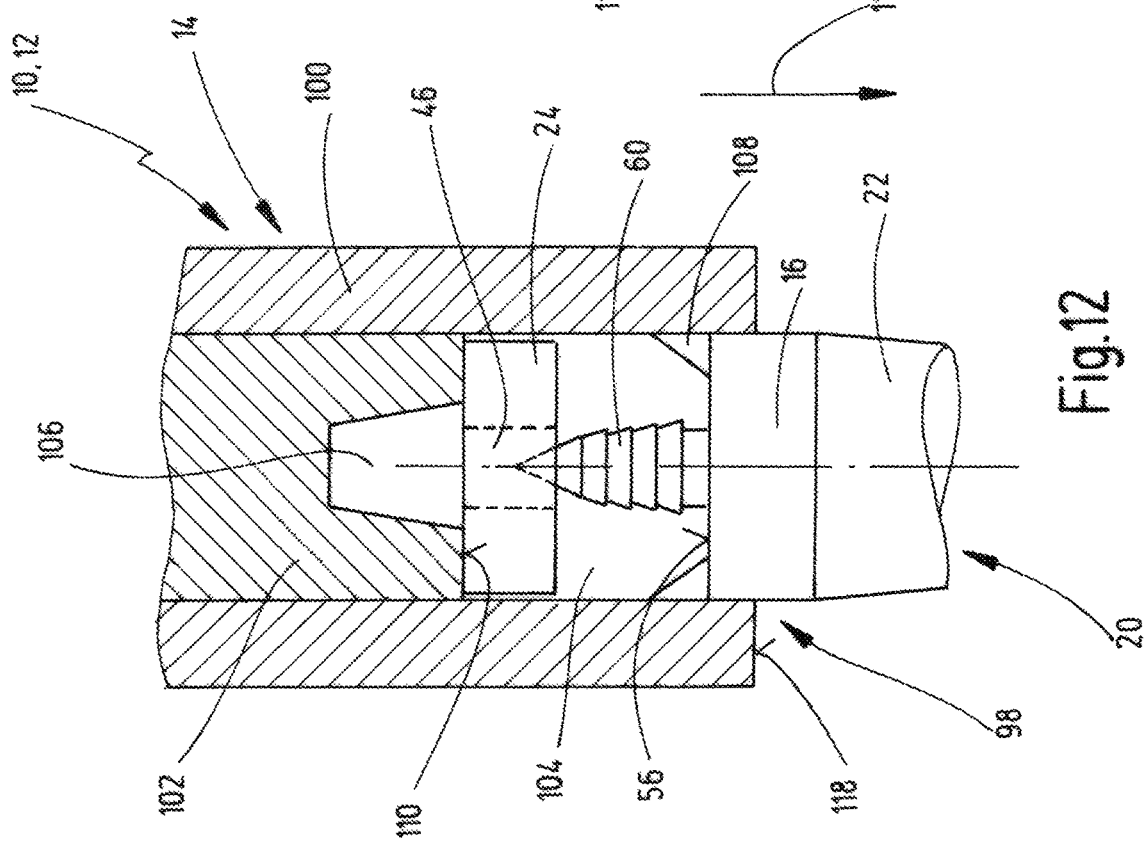

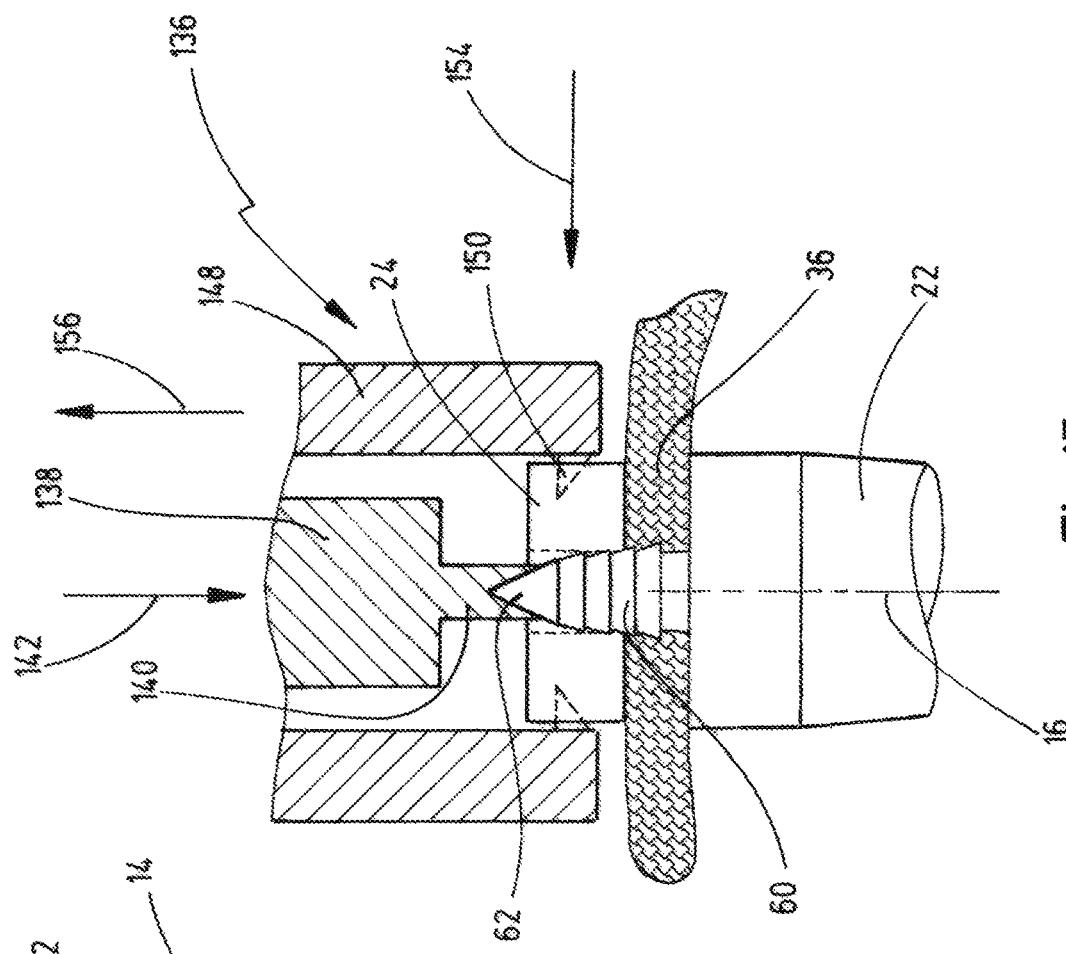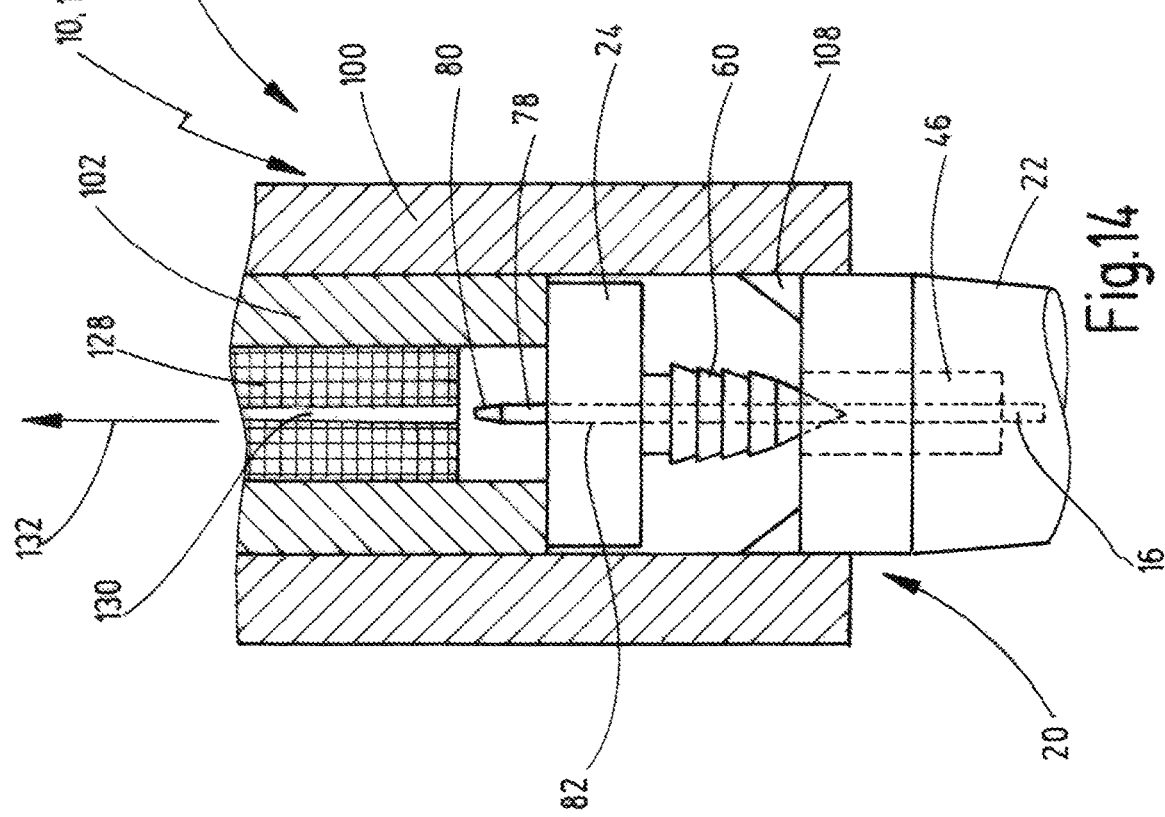

FIXATION UNIT AND HANDLING DEVICE FOR A SUTURE-LESS FIXATION OF TISSUE

This application claims priority from German patent application 10 2016 113 797.9, filed on Jul. 27, 2016. The entire content of that priority application is fully incorporated by reference herewith.

BACKGROUND OF THE INVENTION

Field of the Invention

The present disclosure relates to a fixation unit for a suture-less fixation of tissue at bones, having an anchor element that is arranged to be fixed at a bone, and a retaining element that is arranged to be coupled with the anchor element to attach the tissue section at the bone.

Description of the Background Art

Fixation systems for fixing soft tissue at bones, for instance for fixing muscles, ligaments and such like, are known. For instance, reference is made to the procedure for fixing the rotator cuff at the upper arm bone. Generally, fixation systems of that kind may be used in several arthroscopic, endoscopic and open surgery treatments.

Commonly, the fixation systems comprise an anchor element that is for instance arranged as a percussion dowel or a screw anchor. Conventional fixation systems generally further comprise a suture that is pierced through the tissue to be fixed, for instance, with a needle, and such like. Fixation systems are known, wherein such a suture is then directly or mediately knotted with the anchor. Further, so-called knotless fixation systems are known that utilize sutures for fixation that are, however, clamped so that no knot is necessary.

By way of example, US 2007/0203498 A1 discloses an anchor element for knotless fixation of tissue at a bone by means of at least one suture that is guided through the anchor element, comprising a body, at the outer side of which projections are provided that prevent a pulling-off of the anchor element, that is embedded in the bone, a transverse bore for guiding the at least one suture transversely through the body, wherein the transverse bore is arranged in a distal end portion of the body and extending therethrough, and a clamping element for clamping the suture that runs through the body, wherein the clamping element is moveable along the body.

The anchor element enables a suture based, but, however, knotless fixation of the tissue at the bone. Nevertheless, it is necessary to connect at least three separate attachment elements with one another, namely the anchor as such, the clamping element and the suture pushed therebetween. It is to be noted that the suture has to be formed as an eyelet to be able to grip and secure the tissue.

In the field of arthroscopy and endoscopy, generally in the field of minimally-invasive surgery, there is a general strive to minimize or even entirely avoid potential traumas at the body of the patient. Preferably, access openings to the body that are as small as possible, are formed, through which, however, also the handling of the involved components has to be effectuated. This applies also to the afore-described fixation systems, for instance.

With suture based fixation systems for fixing tissue at bones, it is sometimes necessary to use a plurality of sutures and a plurality of anchors. Further, it is sometimes necessary to lead a suture multiple times through a tissue section to enable and improve force application. Furthermore, due to the limited space, the sutures have to be knotted outside the body and then again have to be inserted through respective cannulas.

In view of this, it is an object of the present disclosure to present a fixation unit for suture-less fixation of tissue at bones that enables a simplified handling.

It is a further object of the present disclosure to present a fixation unit that preferably enables an atraumatic (low trauma or trauma-free) fixation of the tissue.

It is a further object of the present disclosure to present a fixation unit that enables large retaining forces, wherein preferably the surface load at the tissue will not be excessively large.

It is a further object of the present disclosure to present a fixation unit, wherein the formation and the securing of the connection can be preferably accomplished simple and with low errors.

It is a further object of the present disclosure to present a fixation unit that exhibits only a small vulnerability to operation errors.

It is a further object of the present disclosure to present a fixation unit that enables an attachment of the tissue at the bone with a space required for the handling of the involved components that is as small as possible.

It is a further object of the present disclosure to present a fixation unit that enables a reduction of the number of necessary access points to the body and/or the size of the necessary openings for the fixation procedure.

It is a further object of the present disclosure to present a handling device that is provided with a respective fixation unit and that enables the fixation of the tissue section with small efforts.

It is a further object of the present disclosure to present an inspection tool by means of which the connection can be detached, preferably with low trauma.

SUMMARY OF THE INVENTION

In regard of a fixation unit, these and other objects are achieved by a fixation unit for a suture-less fixation of tissue at a bone, wherein the fixation unit comprises an anchor element that is arranged to be fixed to a bone, a retaining element that is arranged to be coupled with the anchor element to attach a tissue section, wherein the anchor element and the retaining element are lockable to one another and form therebetween in a locked state a retaining zone for the tissue section.

In an exemplary embodiment, there is provided a fixation unit for a suture-less fixation of tissue at a bone, wherein the fixation unit comprises an anchor element that is arranged to be fixed to a bone, a retaining element that is arranged to be coupled with the anchor element to attach a tissue section at the anchor element, and a connecting spike that extends from the anchor element, wherein the connecting spike is arranged to extend through the tissue section when the retaining element and the anchor element engage one another, wherein the anchor element and the retaining element are lockable to one another and form therebetween in a locked state a retaining zone for the tissue section, wherein a locking recess is formed at the retaining element, and wherein, in the locked state, the connecting spike at least sectionally extends through the locking recess.

In accordance with some exemplary embodiments of the present disclosure there is namely formed a simple snap-lock connection which may be simply created by pressing the retaining element towards the anchor element. In other words, the locking of the anchor element with the retaining element is accomplished by a movement that has the same direction as the approaching movement of the anchor element and the retaining element. This simplifies the assembling procedure. Further, it is not necessary to provide an excessively large space for applying such a connection.

A defined push movement of the retaining element connects the retaining element, for instance loss-proof, with the anchor element. Similar to a push button or a similar positive-locking and/or force-fitted press connection, basically loss-proof connections may be formed. As the anchor element and the retaining element cooperate with one another in terms of surface, and may clamp therebetween the tissue section, on the one hand, huge forces may be transmitted. This involves, however, only a small traumatic stress of the tissue section. Hence, in certain embodiments, the surface load at the tissue section is greatly reduced, compared to the suture fixation.

A further benefit of the snap-lock connection is that a plurality of locking steps may be provided so that the fixation unit may be flexibly adapted to tissue sections having different thicknesses.

The anchor element and/or the retaining element may be basically formed from resorbable (degradable) or from non-resorbable materials. This may involve, for instance, metals, non-metals, plastics, ceramics, etc. Also with materials that do not have a great specific strength, a reliable connection may be formed as forces may be applied in an areal fashion. The specific load is greatly reduced.

According to an exemplary embodiment, the retaining element is button shaped or plate shaped and provided with a contact surface that is facing the anchor element, wherein the contact surface is, in the locked state, arranged to preload the tissue section towards the anchor element. In some embodiments, the contact surface is at least sectionally provided with elevations.

This measure has the potential benefit that the actually effective contact surface may be further increased. Further, the load on the tissue section between the anchor element and the retaining element may be distributed in terms of surface. The elevations may be formed, for instance, as waves, domes, bulges, and such like. The elevations may involve a pattern.

In accordance with an exemplary embodiment, the anchor element comprises a counter surface that is facing the contact surface, wherein the counter surface and the contact surface define therebetween in the locked state the retaining zone for the tissue section.

Accordingly, between the counter surface of the anchor element and the contact surface of the retaining element, a positive fit zone or a labyrinth may be formed. This applies even in cases when the counter surface and the contact surface do not directly contact one another. As the tissue section is accommodated therebetween, the retaining forces may be greatly improved. The tissue section is at least partially also secured in its position in a positive fit fashion. A further potential benefit of this arrangement is that local extreme loads on the tissue may be reduced or even entirely avoided.

By way of example, the counter surface and the contact surface may comprise patterns that are respectively adapted to one another, wherein elevations on the one part correspond with recesses on the other part.

According to an exemplary embodiment, the counter surface is at least sectionally provided with elevations that are adapted to elevations at the contact surface of the retaining element so that, in the locked state, a labyrinth or a pattern of elevations of the contact surface and elevations of the counter surface is formed. Hence, in certain embodiments, the contact surface and the counter surface are at least sectionally formed to be uneven (non-planar). This may involve, however, an organic shape comprising soft or tangential transitions between single shape elements (elevations, recesses, and such like).

By way of example, a wavy (corrugated) shape comprising peaks and troughs may be provided at the contact surface and the counter surface. Peaks and troughs of the wave may basically extend in a radial direction or in a circular direction (circumferential direction).

A potential benefit of the locking-in of the anchor element and the retaining element is that the contact surface and the counter surface approach one another during the joining procedure, but are not moved with respect to one another in another way, for instance rotated with respect to one another. This has the potential benefit that the desired relative orientation in regard of the surface design of the contact surface and the counter surface is maintained.

In certain embodiments, in this context, the anchor element and the retaining element may be defined in such a way that they are arranged in a fashion torque-proof with respect to one another. In other words, the anchor element and the retaining element may be jointly and absolutely rotated. However, at least in accordance with this embodiment, no relative rotation between the anchor element and the retaining element is permitted.

In accordance with an exemplary arrangement, a snap-lock connection is provided that enables an approaching between the retaining element and the anchor element and that counteracts, in the locked state, a detachment movement between the retaining element and the anchor element.

The snap-lock connection may involve for instance a design element that is pine-tree shaped (fishbone shaped). In other words, the snap-lock connection is formed similar to a nail anchor. Generally, the snap-lock connection may involve locking elements, for instance locking teeth, locking springs, barbs, and such like. Accordingly, the snap-lock connection may define an approaching movement, i.e. an enabled movement, and an opposite blocking direction in which no detachment movement is permitted.

In accordance with an exemplary embodiment, a connection spike is provided that extends between a base body of the retaining element and a shaft of the anchor element. In certain embodiments, the connecting spike is arranged to extend through the tissue section when the retaining element and the anchor element approach one another.

The connecting spike may be pine-tree shaped (fishbone shaped), and may generally have a tapering towards its tip. The connecting spike is arranged to pierce the tissue to be fixed. In this way, the connecting spike on the one hand fixes the tissue section, at least in some respect. On the other hand, the connecting spike connects the retaining element and the anchor element.

In accordance with an exemplary embodiment, the connecting spike is provided with a fluting or circumferential notching that secures the position in the locked state. Accordingly, the connecting spike may form a component of the snap-lock connection. The connecting spike may be pine-tree shaped (fishbone shaped) and provided with a circumferential knurling. Generally, the connecting spike may be formed similar to an anchor nail. However, it is also conceivable to provide differently shaped indents, teeth, and such like at the connecting spike.

In accordance with an exemplary embodiment, the connecting spike cooperates with a locking recess that comprises locking elements. In certain embodiments, the locking elements are formed direction dependent and comprise a blocking direction.

In certain embodiments, the locking elements are arranged as locking springs or locking noses. The locking elements may be locked with the circumferential notching of the connecting spike when the retaining element and the anchor element approach one another. In an opposite blocking direction, the locking elements prevent by means of a positive-lock and/or a force-fit a detachment of the connection. Accordingly, the assembling, i.e. the engagement is relatively simple. The disassembling is all the more difficult. It may be provided that a disassembling is only enabled by destroying the locking elements. The locking elements may also basically be referred to as snap-on or snap-lock elements. Accordingly, the resulting locking connection may also be referred to as snap-coupling.

In accordance with an exemplary embodiment, the connecting spike is formed at the anchor element, for instance as an extension towards the retaining element, wherein at the retaining element a locking recess is formed, wherein in the locked state the connecting spike at least sectionally extends through the locking recess. In accordance with this embodiment, the connecting spike extends from distal to proximal. The retaining element may be mounted at the connecting spike.

In accordance with an exemplary embodiment, the connecting spike is formed at the retaining element, for instance as an extension towards the anchor element, wherein at the anchor element a locking recess is formed, and wherein in the locked state the connecting spike at least sectionally extends through the locking recess. In accordance with this embodiment, the connecting spike extends from proximal to distal. The proximal spike that is formed at the retaining element may be inserted into the locking recess that is provided at the anchor element. This involves a guiding through or piercing through the tissue section.

In accordance with an exemplary embodiment, a guide pin is formed at the anchor element that is arranged as a mounting aid and that extends towards the retaining element, wherein the connecting spike comprises a guide recess into which the guide pin is insertable to move the connecting spike to the locking recess in the anchor element.

This has the potential benefit that the connecting spike that is formed in accordance with this embodiment at the retaining element does not have to be inserted "blindly" into the locking recess. When the anchor element is attached, the tissue section is at least partially placed thereon. This involves that the tissue section may partially or entirely overlap the anchor element. As, however, the guide pin may be pierced through the tissue section, an orientation aid or positioning aid is provided. The connecting spike that is in turn provided with a guide recess may be pushed onto the guide pin and eventually inserted into the locking recess.

In certain embodiments, the guide pin is arranged to be detached and removed after the locking procedure. The guide pin may be formed as a separate part that is detachably attached to the anchor element. It is however also conceivable to arrange the anchor element and the connecting spike as an integrally shaped component. Accordingly, for instance, a predetermined breaking point is provided so that the guide pin is detachable and removable in a defined manner.

In regard of the handling device, the above and further objects are achieved by a handling device for inserting a fixation unit, comprising a mounting tool; and a fixation unit comprising an anchor element that is arranged to be fixed to a bone, and a retaining element that is arranged to be coupled with the anchor element to attach a tissue section at the bone, wherein the anchor element and the retaining element are lockable to one another and form therebetween in a locked state a retaining zone for the tissue section, wherein the mounting tool comprises a shaft assembly having a distal support section at which the fixation unit is mountable, wherein the shaft assembly comprises a first shaft component for taking up the anchor element, and a second shaft component for taking up the retaining element, wherein the anchor element and the retaining element are jointly mountable by the mounting tool in a state axially displaced and disengaged from one another, wherein the first shaft component is arranged to feed the anchor element to the bone, and wherein the second shaft component is arranged to lock the retaining element and the anchor element with one another when the anchor element is fixed.

The mounting tool of the handling device enables a joined feeding of the anchor element and the retaining element that are, however, not yet fixedly connected with one another. The mounting tool is arranged to firstly drive in the anchor element, for instance by a respective pressure (percussion dowel) or by a screwing movement (screw anchor). As the anchor element and the retaining element are supported by different shaft components, it is basically possible to move the anchor element and the retaining element relative with respect to one another. In certain embodiments, the retaining element may be moved to the anchor element to create the snap-lock connection.

The feed direction for the anchor element and the retaining element is the same. In certain embodiments, the shaft assembly of the mounting tool, at least in accordance with some embodiments, has to be inserted into the body only once. It goes without saying that the mounting tool, subsequent to the attachment of the anchor element and the fixation of the anchor element at the bone, is reversed for the moment, i.e. lifted away from the anchor element. This is necessary to place the tissue section to be fixed between the anchor element and the retaining element. Subsequently, the mounting tool is again moved towards the connecting spot (i.e. from proximal to distal), to feed the retaining element to the anchor element. This may involve a piercing of the tissue section.

In accordance with an exemplary embodiment of the handling device, the first shaft component is arranged to transmit at least one of a feed force or a torque to the anchor element, wherein the second shaft component is displaceable relative to the first shaft component to move the retaining element towards the anchor element.

In accordance with this embodiment, the first shaft component is for instance arranged as a hollow shaft. The second shaft component is for instance disposed within the first shaft component. Both shaft components are axially displaceable with respect to one another, in accordance with at least some embodiments. Accordingly, the first shaft component may initially act on the anchor element to fix the anchor element. Subsequently, the retaining element may be mounted.

In accordance with an exemplary embodiment, the handling device further comprises a pull unit that is arranged to disengage a guide pin that is arranged at the anchor element, from the anchor element when the retaining element is coupled with the anchor element. In certain embodiments, the pull unit is associated with or disposed at the shaft assembly. In other words, the pull unit, in at least some embodiments, may be accommodated at the shaft assembly so that the shaft assembly forms a carrier or support for the pull unit.

In this way, using only a single mounting tool, the anchor element may be fixed, the retaining element may be connected and locked with the anchor element, and the guide pin may be detached. This embodiment of the mounting tool is suitable, at least in certain embodiments, for the arrangement of the fixation unit, wherein the connecting spike is arranged at the retaining element and extends towards the anchor element, wherein at the anchor element the guide pin is formed as a mounting aid. However, it is to be noted that not in each case a guide pin a necessary. There are several embodiments that do not implement a guide pin.

A further aspect of the disclosure relates to an inspection tool for a handling device, wherein the inspection tool is arranged for disengaging the retaining element from the anchor element, and wherein the inspection tool is arranged as one of a pulling-off tool or a splitter tool.

Hence, the inspection tool may be arranged similar to a puller or a nut splitter. In certain embodiments, the inspection tool is arranged to radially clamp and/or to radially engage/reach under the retaining element to disengage the retaining element, preferably without or with only low traumatic effects on the tissue, if possible. By way of example, at the retaining element lateral recesses are provided that may be engaged by the inspection tool, for instance by a gripper element or a clamping element.

It is however also conceivable to engage the retaining element primarily in a force-fitted manner. It is further also conceivable to deform the retaining element at least partially to be able to apply the detachment forces. In accordance with at least some embodiments, the inspection tool comprises a downholder that mediately or directly acts on the connecting spike that is arranged at the anchor element, and that serves as a support. In this way, large forces may be applied to the retaining element to disengage the retaining element. However, this does not have negative effects on the position of the anchor element that is, so to say, decoupled by the downholder. In this way, the locking forces of the unidirectional snap-lock connection may be overcome.

It is to be understood that the previously mentioned features and the features mentioned in the following may not only be used in a certain combination, but also in other combinations or as isolated features without leaving the spirit and scope of the present disclosure.

BRIEF DESCRIPTION OF THE DRAWINGS

Further features and advantages of the invention are disclosed by the following description of a plurality of exemplary embodiments, with reference to the drawings, wherein:

FIG. 12 shows a cross-sectional partial view of a support section of a mounting tool at which a fixation unit is mounted, in a first state;

FIG. 13 shows a further view of the arrangement of FIG. 12 in a second state;

FIG. 14 shows a cross-sectional partial view of a support section of a further embodiment of a mounting tool at which a fixation unit is mounted; and FIG. 15 is a cross-sectional partial view of an inspection tool for detaching a retaining element from an anchor element.

DETAILED DESCRIPTION

Figure 1:
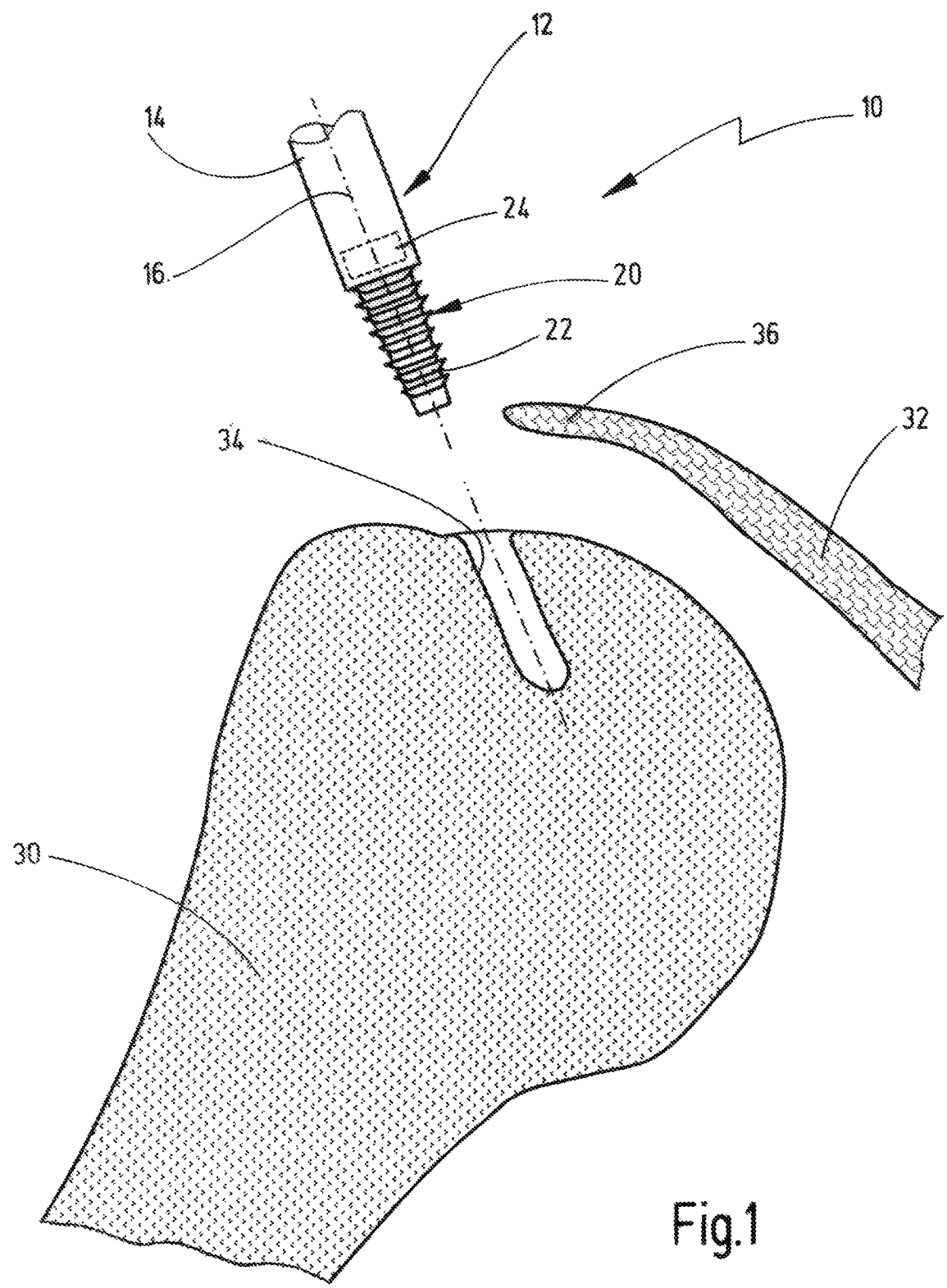
FIG. 1 shows a schematic view for elucidating a field of application of a fixation unit for a suture-less fixation of tissue at a bone.

FIG. 1 elucidates with reference to a schematic, greatly simplified partial view a handling device 10 that is usable for the fixation of soft tissue at bones.

The device 10 comprises a mounting tool 12, wherein in FIG. 1 merely a distal section of a shaft assembly 14 of the mounting tool 12 is illustrated. Generally, at a proximal end of the mounting tool 12, a handpiece is provided, refer also to FIG. 11.

At the shaft assembly 14, a fixation unit 20 is mounted that is merely symbolically illustrated in FIG. 1. The shaft assembly 14 and the fixation unit 20 are aligned along a common longitudinal axis 16. The fixation unit 20 comprises an anchor element 22 and a retaining element 24. The anchor element 22 protrudes at a distal end of the shaft assembly 14 beyond the shaft assembly 14. The retaining element 24 is arranged proximal of the anchor element 22. The anchor element 22 may generally be arranged as a percussion dowel or a screw anchor.

FIG. 1 further shows with reference to a schematic cross-sectional partial view a bone 30 and tissue 32 that is detached from the bone 30. The tissue 32 may involve, for instance, a section of the so-called rotator cuff. Accordingly, the bone 30 may involve an upper arm bone. In an unhurt state, the tissue 32 is naturally fixed at the bone 30. However, at the tissue 32, damages may occur, for instance ruptures, and such like. This may result in a state were a tissue section 36 is detached from the bone 30.

The tissue section 36 can be fixed at the bone 30 when the anchor element 22 is inserted into a retaining recess 34 at the bone 30. This means in other words that the bone 30 is at least sectionally exposed to form the retaining recess 34, for instance by boring and/or milling. The tissue section 36 to be fixed is sectionally turned back or pushed aside. Thereafter, the anchor element 22 may be fixed in the retaining recess 34. Subsequently, the tissue section 36 may be fixedly attached to the bone 30 with the addition of the retaining element 24 when the retaining element 24 is appropriately connected with the anchor element 22.

In other words, in the fixed state, the tissue section 36 is mounted between the anchor element 22 and the retaining element 24.

As shown herein, in accordance with at least some embodiments, the retaining recess 34 is a blind recess, i.e. the retaining recess 34 does not fully extend through the bone 30 to form a through hole. This requires that the anchor element 22, is spite of being shaped as a dowel like element for the insertion into blind holes, is arranged to provide a considerable holding force to ensure a reliable fixation of the tissue section 36.

Generally, to keep the trauma as small as possible when fixing the tissue section 36 at the bone 30, minimally-invasive arthroscopic and/or endoscopic procedures are used. It is desirable that both the anchor element 22 and also the retaining element 24 of the fixation unit 20 can be fed to the retaining recess 34 with only a single mounting tool 12. Hence, it is not necessary to insert an additional tool when the anchor element 22 is applied to feed the retaining element 24 to the anchor element 22.

In the context of the present disclosure, the term proximal side and/or proximal surface shall be understood as that side or surface that is facing the surgeon during the handling of the fixation unit 20. Accordingly, the term distal surface or distal side is to be understood as that surface or side that is facing away from the surgeon. Generally, distal elements or sections are spaced further away from the surgeon than proximal elements or sections.

The fixation unit 20 comprising the anchor element 22 and the retaining element 24 that is merely schematically shown in FIG. 1 will be elucidated in more detail with reference to FIGS. 2 to 5 that illustrate a first exemplary embodiment, and with reference to FIGS. 6 to 9 that illustrate a further exemplary embodiment.

Figure 2:
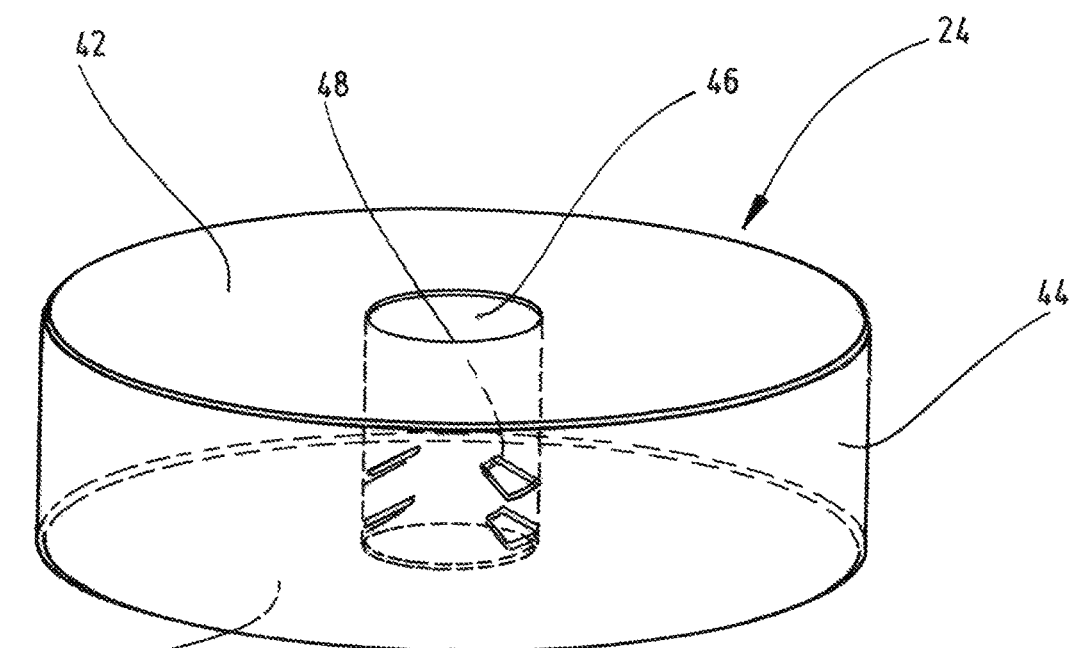
FIG. 2 shows a perspective lateral view of a retaining element of a fixation unit.
Figure 3:
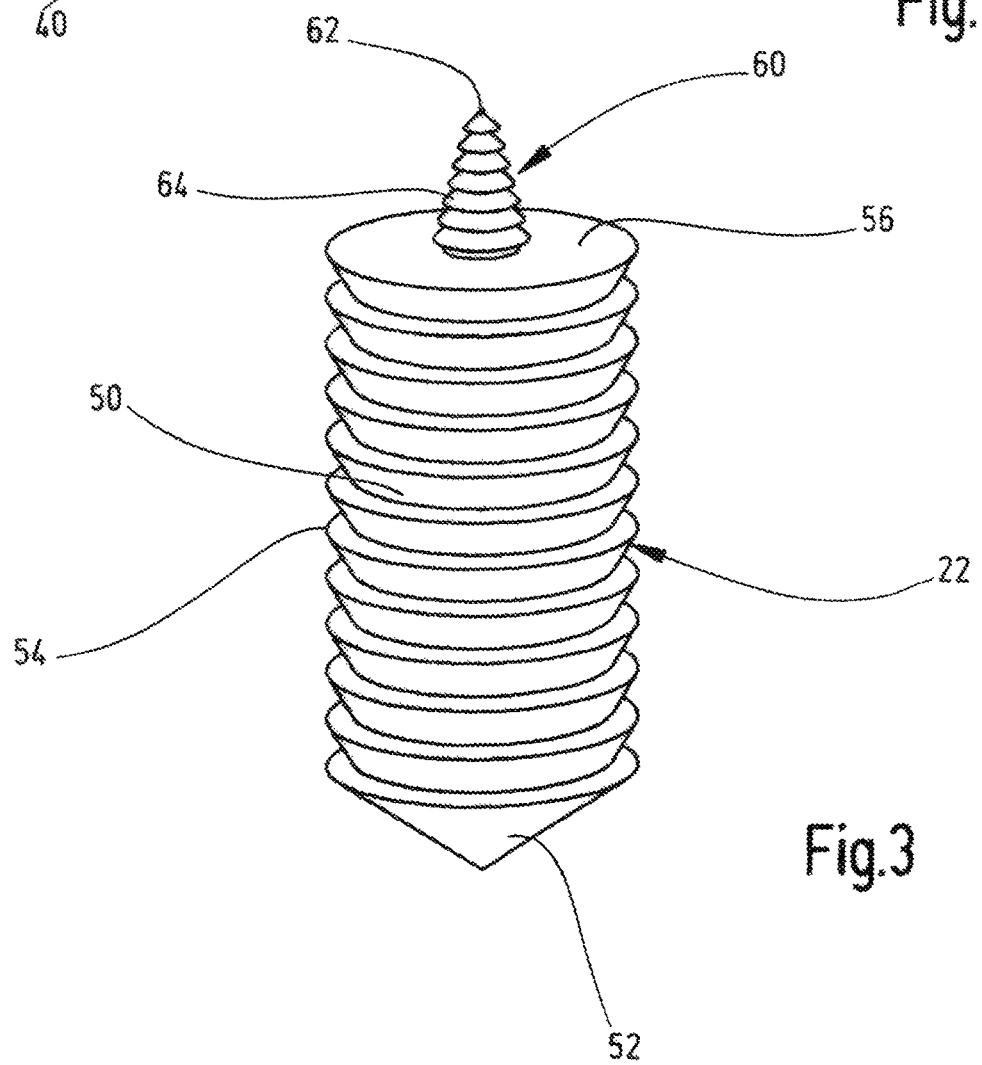
FIG. 3 shows a perspective view of an anchor element of a fixation unit, wherein different scales are used in FIGS. 2 and 3.
Figure 4:
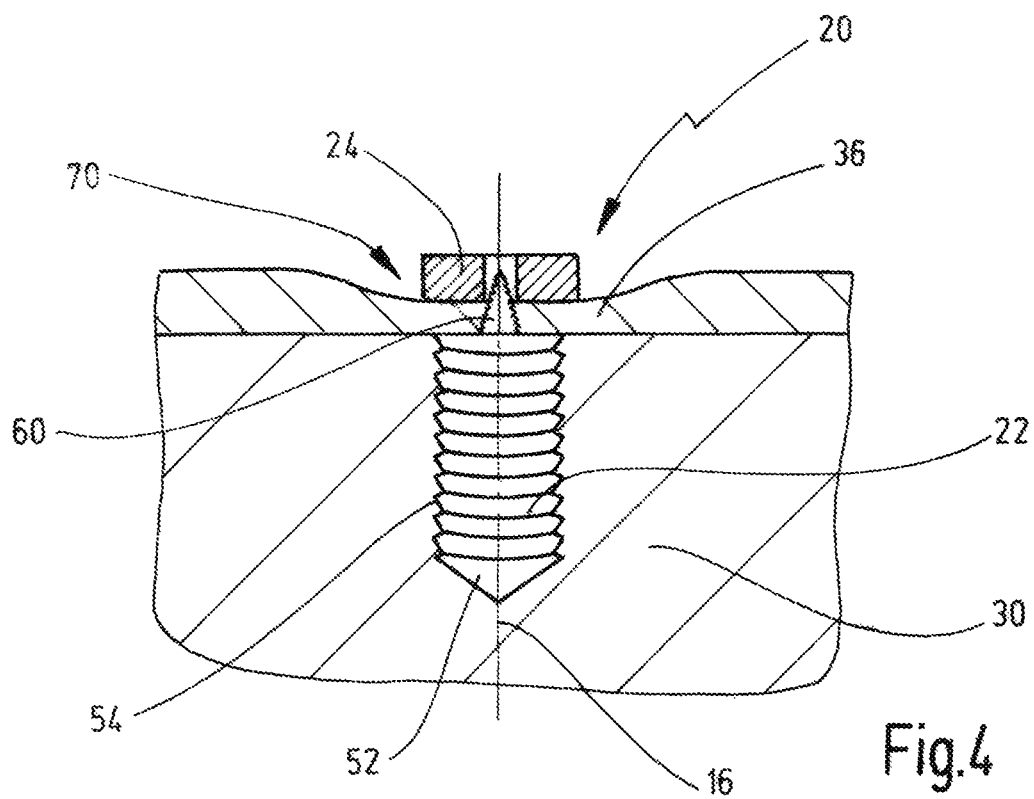
FIG. 4 shows a lateral cross-section through a mounted fixation unit, wherein a retaining element in accordance with FIG. 2 is locked with an anchor element in accordance with FIG. 3.
Figure 5:
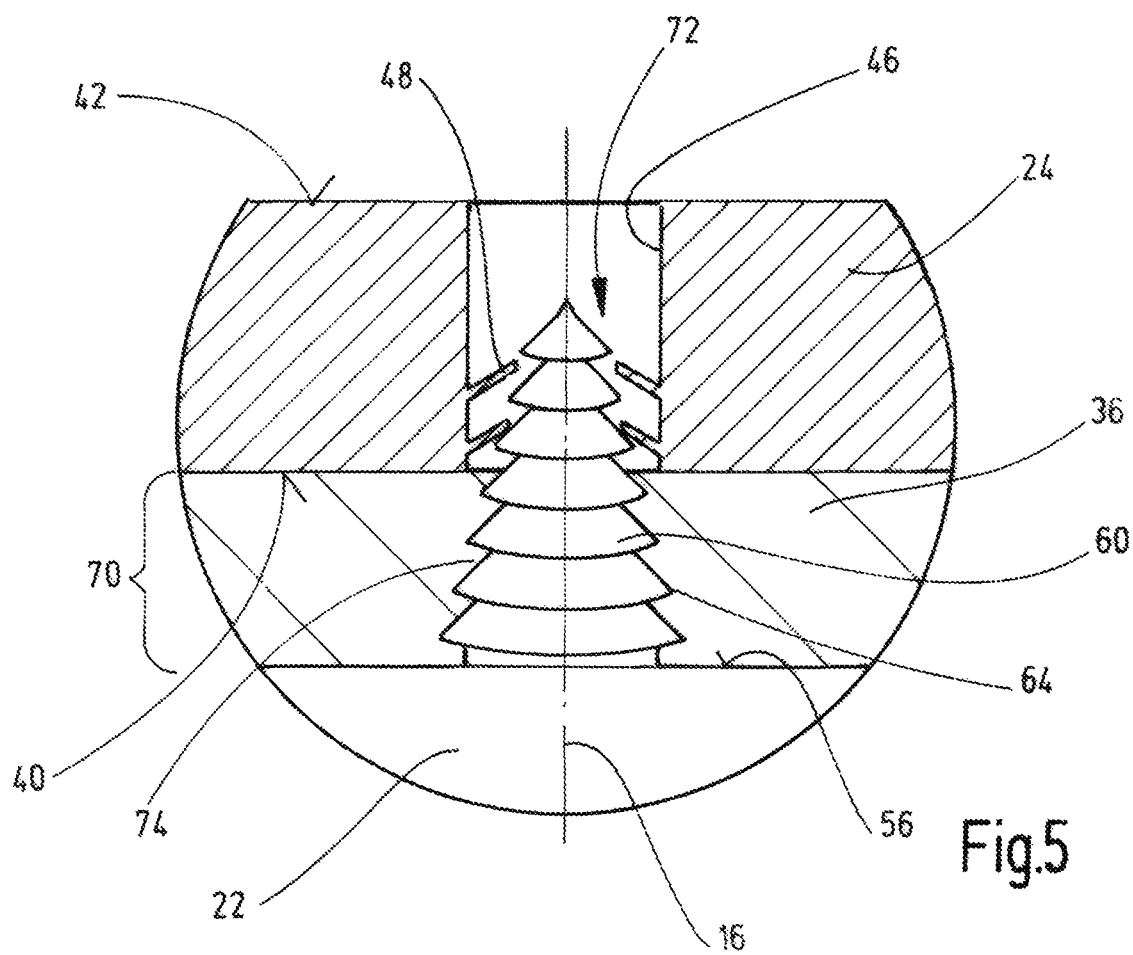
FIG. 5 shows an enlarged partial view of the arrangement of FIG. 4 in the region of a snap-lock connection between the anchor element and the retaining element.

FIG. 1 elucidates a perspective view of a retaining element 24 of a fixation unit 20. FIG. 3 shows a corresponding perspective view of an associated anchor element 22. The illustrations in FIGS. 2 and 3 are not based on identical scales. The retaining element 24 illustrated in FIG. 2 is shown in a larger magnification than the anchor element 22 illustrated in FIG. 3. FIGS. 4 and 5 elucidate the fixation unit 20 with the anchor element 22 and the retaining element 24 in the engaged state, wherein FIG. 5 is an enlarged partial view of the illustration according to FIG. 4.

The fixation unit 20 is arranged as suture-less fixation unit. This involves that no separate suture and, in certain embodiments, no other separate mounting aid is necessary to fix the tissue section 36 at the bone 30, refer also to FIG. 1.

The retaining element 24 is button shaped or disc shaped. The retaining element 24 comprises a contact surface 40 that faces the anchor element 22 in the joined state. A surface of the retaining element 24 that is facing away from the contact surface 40 is referred to as end surface 42. A base body 44 of the retaining element 24 extends between the contact surface 40 and the end surface 42. The contact surface 40 may also be referred to as distal surface. The end surface 42 may also be referred to as proximal surface.

In accordance with the embodiment illustrated with reference to FIGS. 2 to 5, the retaining element 24 further comprises a locking recess 46 that extends through the base body 44. The locking recess 46 may also be referred to as central opening or central bore. In the locking recess 46, locking elements 48 are arranged, that are formed as locking noses, barbs, and suchlike. In certain embodiments, the locking elements 48 are arranged direction dependent and define a feeding direction in which the retaining element 24 is fed to the anchor element 22, and a retaining direction or locking direction that corresponds to a detachment or removal of the retaining element 24 from the anchor element 22.

In accordance with the embodiment illustrated in FIG. 2, four locking elements 48 are arranged in the locking recess 46 (in FIG. 2 merely shown in a hidden view mode). It goes without saying that other configurations regarding the number and/or the arrangement of the locking elements 48 are conceivable.

FIG. 3 elucidates the anchor element 22 that cooperates with the retaining element 24. The anchor element 22 comprises a shaft body 50 at the distal end of which a tip 52 is formed. At the shaft body 50 there is further formed a fixture contour 54 having fixture projections. Accordingly, the anchor element 22 is arranged as a percussion dowel. It goes without saying that the fixture contour 54 may generally also comprise a helical thread or similar mounting elements, in accordance with alternative embodiments. A longitudinal extension of the anchor element 22 is generally adapted to a depth extension on the retaining recess 34 that is formed in the bone 30.

At the proximal end of the shaft body 50, a counter surface 56 is formed. In certain embodiments, in the attached state of the anchor element 22, refer also to FIG. 4 and FIG. 5, the counter surface 56 ends flush or nearly flush with respect to a surface of the bone 30. The counter surface 56 is facing the contact surface 40 of the retaining element 24, at least in the mounted state.

In accordance with the embodiment illustrated with reference to FIGS. 2 to 5, the anchor element 24 further comprises at its proximal end a connecting spike 60. The connecting spike 60 is tapered towards the locking recess 46. The connecting spike 60 comprises a tip 62 that is arranged in accordance with at least some embodiments to pierce or cut through the tissue section 36 (FIG. 1) to pass the connecting spike 60 through the tissue section 36.

The connecting spike 60 further comprises a fixture contour or locking contour, for instance in the shape of a circumferential notching 64. In other words, by way of example, at the connecting spike 60, projections are formed that are adapted to the locking elements 48 of the locking recess 46 in such a way that an undercut snap connection or locking connection is formed when the connecting spike 60 engages the locking recess 46. In this way, the anchor element 22 and the retaining element 24 may be simply joined with one another by means of a snap connection, similar to a pushbutton. The connecting spike 60 extends through the tissue section 36 to be fixed. The tissue section 36 is accommodated in the joined state between the contact surface 40 and the counter surface 56 and hence fixed at the bone 30.

There is no suture or other aid necessary to fix the tissue section 36 at the bone 30. By means of merely two elements, the anchor element 22 and the retaining element 24, the tissue section 36 may be reliably retained at the bone which is accompanied by only a small trauma of the tissue 32. The joined state of the fixation unit 20 will be elucidated with reference to FIGS. 4 and 5.

The anchor element 22 and the retaining element 24 form in the locked state a retaining zone 70 that extends between the contact surface 40 and the counter surface 56. In the retaining zone 70, the tissue section 36 is accommodated. A potential benefit of this arrangement is that at the tissue section 36 only a relatively low surface pressure is present so that overall the point load may be greatly reduced.

FIG. 5 elucidates with reference to an enlarged partial view a resulting snap-lock connection 72 between the anchor element 22 and the retaining element 24. The snap-lock connection 72 comprises a respective locking contour at the connecting spike 60 and in the locking recess 46, for instance locking elements 48 that cooperate with a circumferential notching 64, for instance with some projections thereof.

The shape of the snap-lock connection 72 defines an assembly direction in which a relative movement between the anchor element 22 and the retaining element 24 along the longitudinal axis 16 is basically enabled. There is further an opposite blocking direction which may also be referred to as detachment direction. The locking elements 48 counteract a movement in the detachment direction in an inhibiting and/or blocking manner. Hence, the locking elements 48 thus operate like an arrangement of barbs, for instance.

In FIG. 5, reference numeral 74 elucidates a tissue opening and/or an incision through which the connecting spike 60 extends. In certain embodiments, the tissue opening 74 is formed by the connecting spike 60 itself, for instance by its tip 62 (FIG. 3). In other words, the connecting spike 60 may be pushed through the tissue section 36 to form the tissue opening 74.

A further potential benefit of the arrangement of the anchor element 22 and the retaining element 24 in accordance with at least some embodiments is that the retaining zone 70 does not have to comprise a predefined thickness (and/or height). The snap-lock connection 72 defines a plurality of possible relative positions in which the anchor element 22 and the retaining element 24 may be locked with one another. In other words, the snap-lock connection 72 enables a re-tensioning of the connection between the anchor element 22 and the retaining element 24. A result is that the fixation unit 20 does not have to be adapted to a present thickness of the tissue section 36 with high precision. This increases the flexibility.

With reference to FIGS. 2 to 5, an embodiment of the snap-lock connection will be elucidated wherein the connecting spike 60 is associated with the anchor element 22, and wherein the locking recess 64 is associated with the retaining element 24. Nevertheless, generally also a reverse association is conceivable. A respective exemplary arrangement will be elucidated hereinafter with reference to FIGS. 6 to 9.

Figure 6:
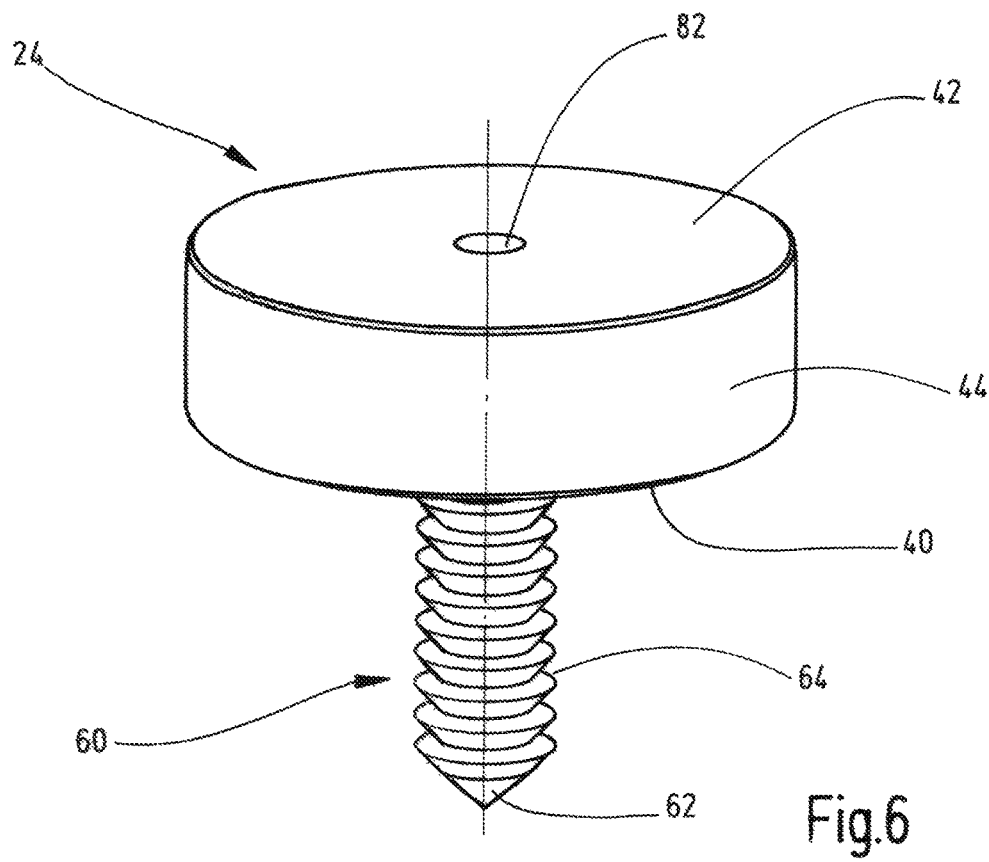
FIG. 6 shows a perspective lateral view of a retaining element of a fixation unit.
Figure 7:
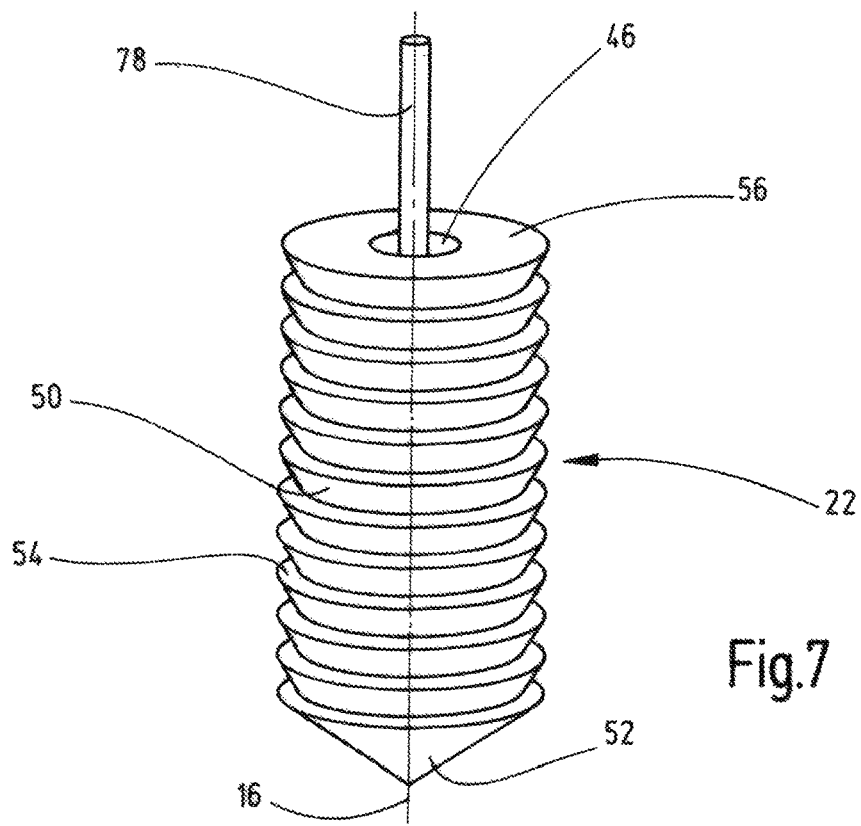
FIG. 7 shows a perspective view of an anchor element of a fixation unit, wherein different scales are used in FIGS. 6 and 7.

As with FIGS. 2 and 3, also FIGS. 6 and 7 elucidate a retaining element 24 and an anchor element 22 of a fixation unit 20. The retaining element 24 is provided with a contact surface 40 and an end surface 42 that are facing away from one another, wherein the contact surface 40 is arranged at a distal side, and wherein the end surface 42 is arranged at a proximal side. Between the contact surface 40 and the end surface 42, a base body 44 extends.

The anchor element 22 elucidated in FIG. 7 comprises a shaft body 50 having a tip 52 and a fixture contour 54. At the proximal-side end of the shaft body 50, a counter surface 56 is formed that defines, in the locked state of the anchor element 22 and the retaining element 24, together with the contact surface 40 a retaining zone 70, refer also FIG. 8 and FIG. 9.

In contrast to the embodiment elucidated with reference to FIGS. 2 to 5, with the embodiment elucidated with reference to FIGS. 6 to 9, the connecting spike 60 is associated with the retaining element 24. Accordingly, the locking recess 46 is associated with the anchor element 22.

The connecting spike 60 extends from the contact surface 40 towards the anchor element 22, i.e. towards a distal end of the fixation unit 20. In contrast thereto, the connecting spike 60, in the embodiment illustrated with reference to FIGS. 2 to 5, extends from the counter surface 56 towards the retaining element 24, i.e. towards a proximal end of the fixation unit 20. The connecting spike 60 is arranged to be basically similar to a ribbed nail or an anchor nail. The circumferential notching 64 may be basically also helically formed, i.e. similar to a thread.

With the embodiment of the fixation unit 20 elucidated with reference to FIGS. 6 to 9, it has to be observed that the tissue section 36 to be attached has to be pierced or penetrated by the connecting spike 60 from proximal to distal, i.e. towards the anchor element 22. As, however, the tissue section 36 at least sectionally covers the anchor element 22, it is possibly difficult to "find" the locking recess 46 with the connecting spike 60. This has to be accomplished, so to say, "blindly". Generally, the tip 62 may serve as an insertion aid to find the locking recess 46.

Figure 8:
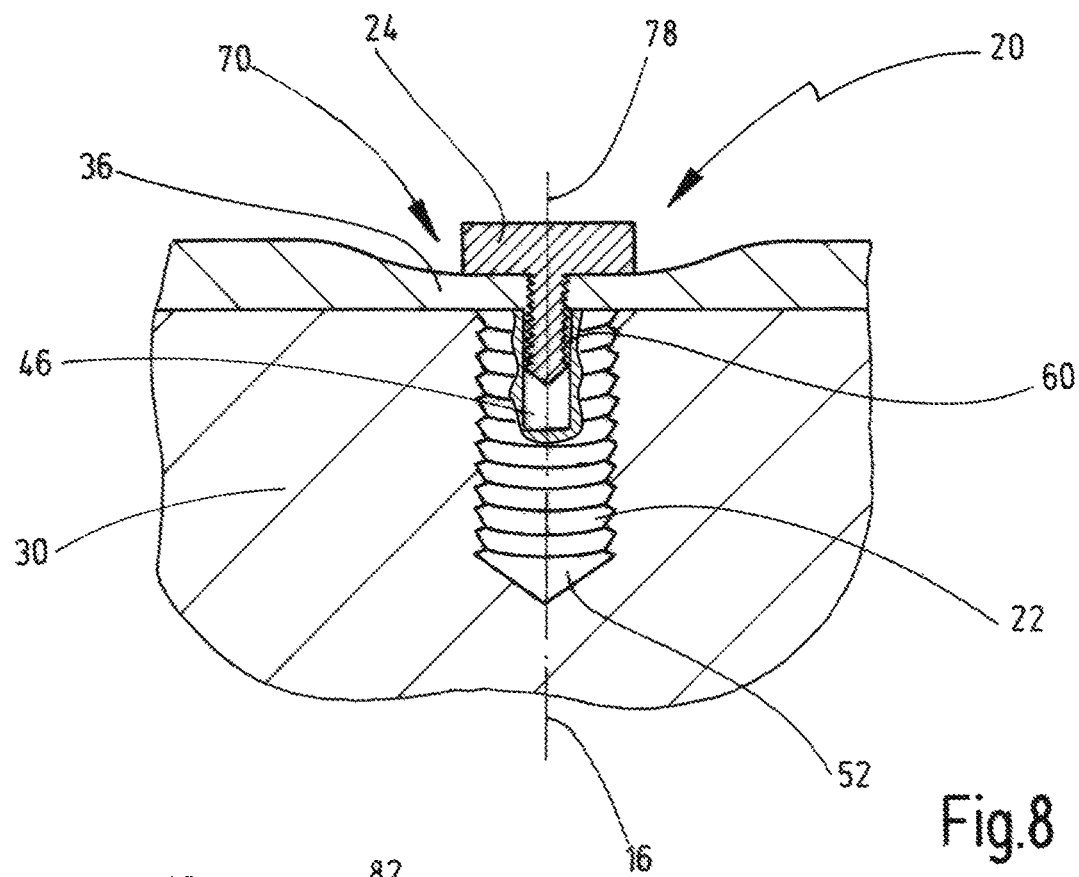
FIG. 8 shows a lateral cross-section through a mounted fixation unit, wherein a retaining element in accordance with FIG. 6 is locked with an anchor element in accordance with FIG. 7.

Nevertheless, in accordance with at least some embodiments, a facilitated mounting of the retaining element 24 is intended by providing a guide pin 78 that is associated with the anchor element 22. The guide pin 78 is mounted in the locking recess 46 at the anchor element 22, but does not entirely occlude the locking recess 46. In other words, a radial extension and/or a diameter of the guide pin 78 is significantly smaller than a radial extension and/or a diameter of the locking recess 46. In this context, reference is also made to the enlarged partial view of the arrangement according to FIG. 8 shown in FIG. 9. The guide pin 78 is provided with a tip 80 (FIG. 9), for instance. A guide recess 82 that extends in the retaining element 24 is associated with the guide pin 78. The guide recess 82 is formed in the embodiment in accordance with FIGS. 6 to 9 as a through-hole bore in the retaining element 24 that extends through the base body 44 and through the connecting spike 60.

The guide pin 78 serves as an orientation aid. Having attached the anchor element 22, the tissue section 36 may be positioned above the anchor element 22. This may involve that the guide pin 78 pierces the tissue section 36. Thereafter, the guide pin 78 is "visible" and/or "noticeable" for the retaining element 24. The retaining element 24 and the connecting spike 60 may be correspondingly positioned so that the guide recess 82 may be put over the guide pin 78. This involves an alignment of the connecting spike 60 and the retaining element 24 in a desired relative orientation with reference to the anchor element 22. Hence, any elements 22, 24, 60 are concentrically aligned with respect to the longitudinal axis 16 and may be joined with one another.

By way of example, the guide pin 78 is arranged as a separate component and joined with the shaft body 50 of the anchor element 22. It is however also conceivable to integrally form the shaft body 50 and the guide pin 78 wherein it is possible to include predetermined breaking points and such like.

Figure 9:
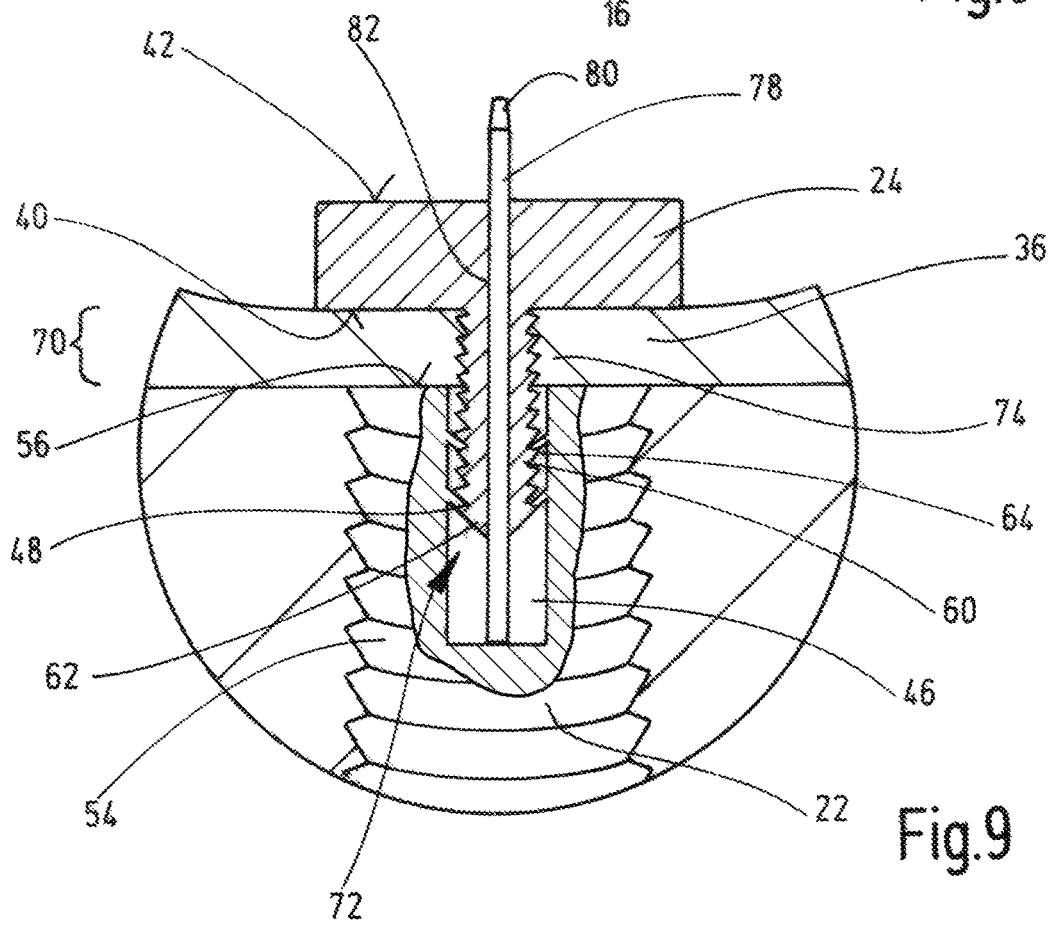
FIG. 9 shows an enlarged partial view of the arrangement of FIG. 8 in the region of a snap-lock connection between the anchor element and the retaining element.

FIGS. 8 and 9 elucidate a joined state, wherein the anchor element 22 and the retaining element 24 define therebetween a retaining zone 70 in which a tissue section 36 is received. Similar to the arrangement already shown in FIG. 5, a snap-lock connection 72 between the connecting spike 60 and the locking recess 46 is formed also in FIG. 9, for instance between the circumferential notching 64 and the locking elements 48. This is not altered by the basically reverse assignment of the connecting spike 60 and the locking recess 46.

In the retaining zone 70, the tissue section 36 comprises a tissue opening 74 through which the connecting spike 60 extends. The locking elements 48 are arranged in such a way and cooperate in such a way with the circumferential notching 64 that an insertion of the connecting spike 60 into the locking recess 46 is enabled, but that a pulling out of the connecting spike 60 of the locking recess 46 is inhibited or even blocked.

The snap-lock connection 72 for fixing the tissue section 36 at the bone 30 may be accomplished simply. In certain embodiments, a potential benefit is that the locking movement for the fixation of the connection is unidirectional with the feeding movement of the involved components 22, 24. This simplifies the handling of the fixation unit 20 greatly. Dispensing with a suture or a similar aid for fixation has the further potential benefit that in the interior of the body only little space for handling the fixation unit 20 is required. This further contributes to the prevention, at least to the minimization, of potential traumas.

Figure 10:
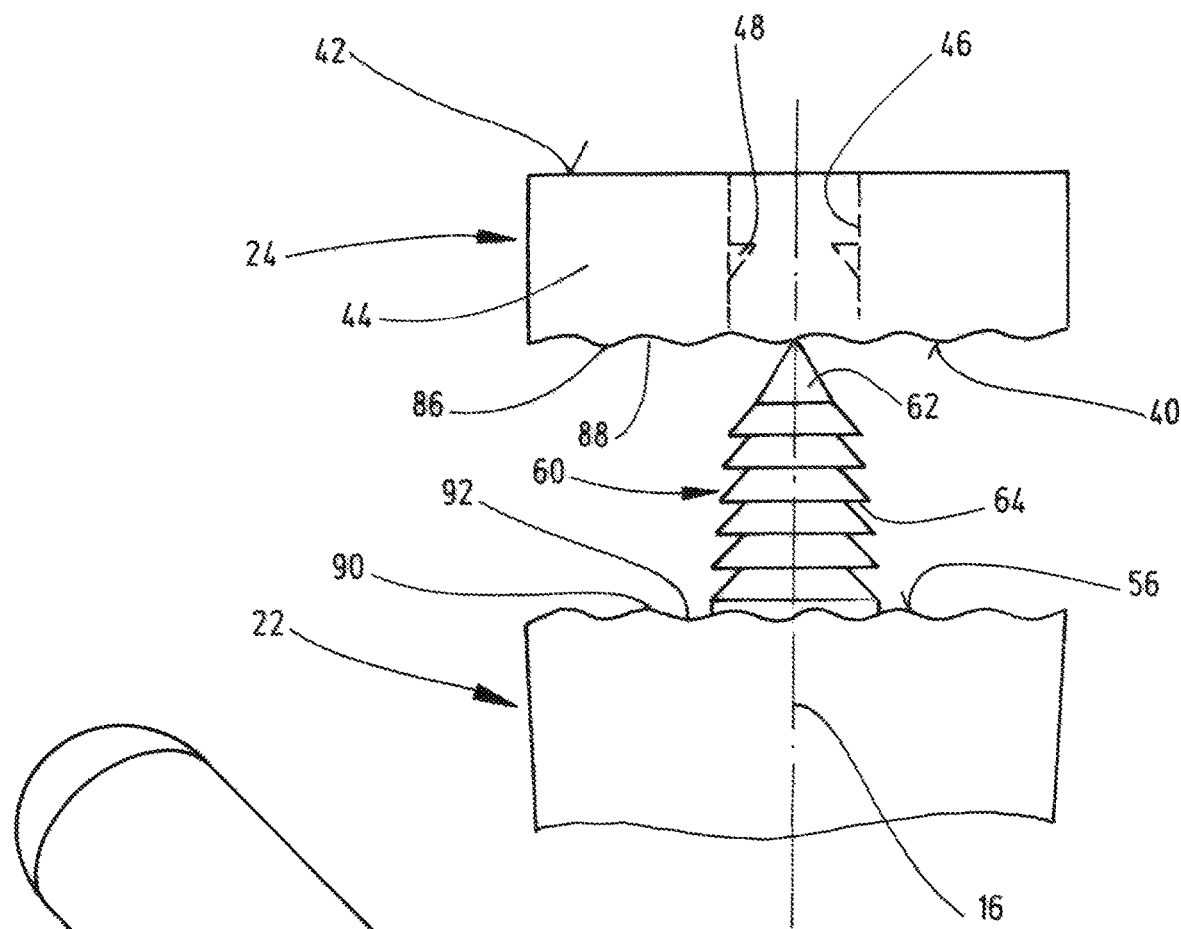
FIG. 10 shows a schematic lateral view of a further fixation unit having an anchor element and a retaining element that are illustrated in a non-engaged state, for elucidating contact surfaces.

FIG. 10 elucidates with reference to a schematic partial illustration in a lateral view a further exemplary embodiment of a fixation unit 20 having features that may be basically combined with the afore-described embodiments.

The fixation unit 20 comprises an anchor element 22 and a retaining element 24 that may be locked or snap-fitted with one another by means of a connection that comprises a connecting spike 60 and a locking recess 46. In the locking recess 46, locking elements 48, for instance in the form of barbs are formed that cooperate with a circumferential notching 64 at the connecting spike 60. It is generally also conceivable to form locking elements that are hook shaped, barb shaped or that have a similar shape at the connecting spike 60, and to form a circumferential notching, accordingly, in the locking recess 46.

At the retaining element 24, a contact surface 40 is formed that cooperates with a counter surface 56 at the anchor element 22 to fix a tissue section 36 between the anchor element 22 and the retaining element 24, refer also to FIGS. 4, 5 and 8, 9.

It is intended in accordance with at least some embodiments to form the contact surface 40 and/or the counter surface 56 not entirely flat as a circular surface or an annular surface having a substantially flat extension.

Instead, the contact surface 40 may be provided with elevations 86 that may alternate with recesses 88, for instance. Similarly, also the counter surface 56 may be provided with elevations 90 that alternate with recesses 92. Accordingly, the contact surface 40 and/or the counter surface 56 may be at least sectionally corrugated (wavelike). Other types of elevations 86, 90 and/or recesses 88, 92 may be readily envisaged. This may involve, for instance, dome-shaped elevations, trough-shaped depressions, tips, lowerings, and such like.

In certain embodiments, the contours of the contact surface 40 and the counter surface 56 are adapted to one another so that in the joined, locked state elevations 86 of the contact surface 40 are associated with recesses 92 of the counter surface 56. The same applies to elevations 90 of the counter surface 56 that are associated with recesses 88 at the contact surface 40.

Due to the deliberately non-flat arrangement of the contact surface 40 and the counter surface 56, the traumatic stress of the clamped-in tissue section 46 may be further reduced. In certain embodiments, an increase of the effective contact surface may be achieved. Further, due to the uneven arrangement of the contact surface 40 and the counter surface 56 that correspond with one another, an increase in the (lateral) retaining forces is achieved as, so-to-say, the friction between the tissue section 36 and the adjacent surfaces 40, 56 is increased by a respective labyrinth shape or positive-fit shape.

By way of example, the contact surface 40 and the counter surface 56 comprise a wave-shaped contour or a corrugated contour that extends radially, departing from the longitudinal axis 16, to the outside. In other words, wave peaks and wave troughs extend star-shaped to the outside. However, also an arrangement is conceivable wherein adjacent wave peaks and wave troughs are concentrically and annularly arranged with respect to one another. Deviating patterns and design elements are of course conceivable. It is basically also conceivable to provide respective contours with elevations 86, 90 only at the contact surface 40, or at the counter surface 56.

Figure 11:
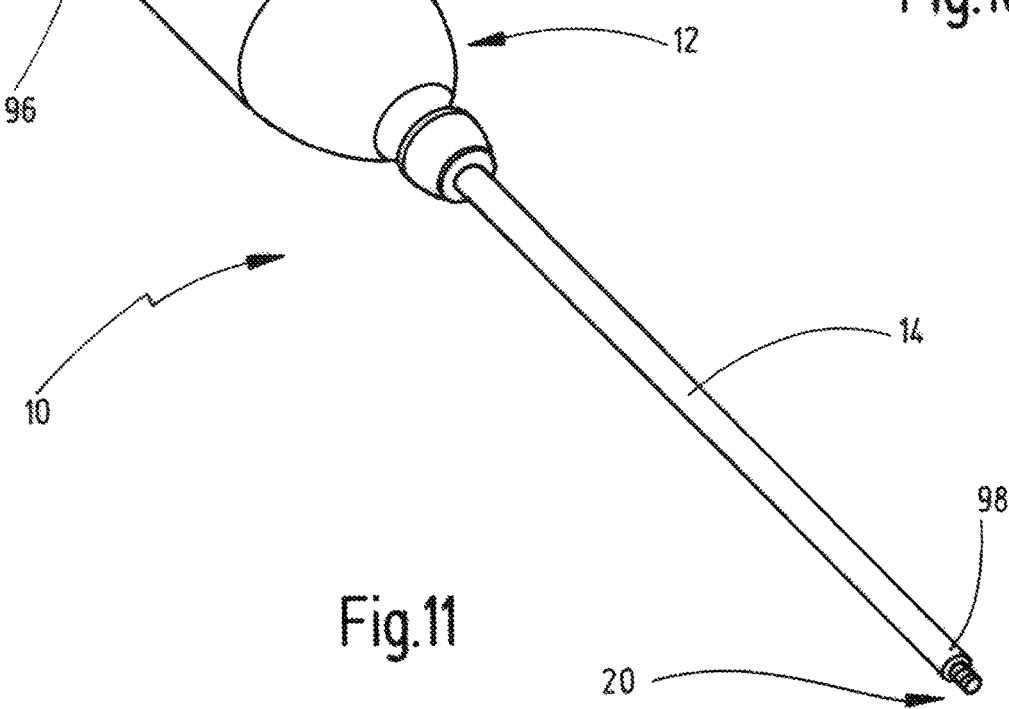
FIG. 11 shows a perspective frontal view of a handling device comprising a mounting tool for inserting a fixation unit.

FIG. 11 elucidates a perspective view of a handling device that is overall designated by 10, and that comprises a mounting tool 12 and a fixation unit 20 that is supported at the mounting tool 12. In this context, reference is also made to the partial view of FIG. 1. The fixation unit 20 is arranged, for instance, in accordance with the embodiments that are illustrated with reference to FIGS. 2 to 10. The mounting tool 12 comprises a handpiece 96 that defines a proximal end of the mounting tool 12. Further, a shaft assembly 14 is provided that extends from the handpiece 96 towards a distal end. The shaft assembly 14 comprises a support section 98 at which the fixation unit 20 is mountable.

In certain embodiments, the mounting tool 12 is arranged to attach both the anchor element 22 and also the retaining element 24. This involves an insertion of the anchor element 22 in the bone 30, refer again to FIG. 1. The fixation of the retaining element 24 further involves a locking of the retaining element 24 with the anchor element 22 attached beforehand. This is accomplished with the involvement of a tissue section 36.

Exemplary arrangements of the mounting tool 12 will be elucidated hereinafter with reference to the embodiment illustrated in FIGS. 12 and 13, and with reference to the embodiment illustrated in FIG. 14.

FIG. 12 and FIG. 13 show a cross-sectional partial view of the support section 98 of the shaft assembly 14. Further, a fixation unit 20 that comprises an anchor element 22 and a retaining element 24 is assigned to the respectively illustrated handling device 10.

The anchor element 22 and the retaining element 24 are mounted at the support section 98 of the shaft assembly 14. FIG. 12 shows a state of the mounting tool 12 in which the anchor element 22 and the retaining element 24 are retained in a defined way spaced away from one another. In this state, both the anchor element 22 and also the retaining element 24 may be moved towards the bone 30. It is, however, not yet intended to lock the anchor element 22 and the retaining element 24 with one another in this state. Rather, this state of the support section 98 is primarily intended to fix the anchor element 22.

The shaft assembly 14 comprises a first shaft component 100 and a second shaft component 102 that are arranged to be moved with respect to one another. By way of example, the first shaft component 100 is arranged as an outer component, and the second shaft component 102 is arranged as an inner component. The second shaft component 102 is arranged in the interior of the first shaft component 100. The anchor element 22 is mounted at the first shaft component 100. The retaining element 24 is mounted at the second shaft component 102. The second shaft component 102 is axially displaced with respect to the first shaft component 100. In this way, a recess 104 is formed in which the retaining element 24 and the connecting spike 60 are accommodated. Nevertheless, no snap-lock connection between the locking recess 46 and the connecting spike 60 is present in the state shown in FIG. 12.

In the second shaft component 102, a recess 106 is formed, for instance, into which the connecting spike 60 may be plunged when the retaining element 24 is locked with the anchor element 22 due to a relative movement of the second shaft component 102 with respect to the first shaft component 100.

At the first shaft component 100, for instance, drivers 108 are formed that engage the anchor element 22. By way of example, the drivers 108 contact the counter surface 56 at the anchor element 22. In this way, by moving the shaft assembly 14 in a feeding direction 114, the anchor element 22 may be fixed in a retaining recess 34 at the bone 30.

Embodiments are conceivable wherein the anchor element 22 is arranged as a percussion dowel. Accordingly, the mounting tool 12 primarily serves for the purpose of pressing-in the anchor element 22 at high pressure. However, also alternative embodiments are conceivable, wherein the anchor element 22 is arranged as a screw anchor. Accordingly, with these embodiments, the mounting tool 12 is arranged to transmit a torque to the anchor element 22, to screw-in the anchor element 22. This may nevertheless be combined with a feed force.

In FIGS. 12 and 13, there is further a frontal pressure surface at the second shaft component 102 designated by 110. A distal frontal surface of the first shaft component 100 is designated by 118. In certain embodiments, the mounting tool 12 with the shaft assembly 14 is arranged in such a way that the anchor element 22 may be inserted into the retaining recess 34 in a bone 30 in such a way that the counter surface 56 ends flush with a surface of the bone 30. This may involve a correspondingly adapted design of the distal end and/or the frontal surface 118 of the first shaft component 100.

FIG. 13 elucidates a state wherein the anchor element 22 is already fixed at the bone 30 (not shown). Further, a tissue section 36 is placed beyond the anchor element 22, wherein the connecting spike 60 perforated the tissue section 36 with its tip 62 to form a tissue opening 74. In this state, the first shaft component 100 is axially moved back in the proximal direction with respect to the second shaft component 102. In other words, the second shaft component 102 is displaced from the first shaft component 100 in the distal direction towards the anchor element 22, refer to a corresponding directional arrow 122 that elucidates an assembling direction and/or locking direction.

The second shaft component 102 contacts the end surface 42 at the retaining element 24 with this abutment surface/pressure surface 110, and pushes the surface 110 towards the anchor element 22. This involves an engagement of the connecting spike 60 with the locking recess 46. FIG. 13 shows a state wherein the retaining element 24 does not yet entirely contact the tissue section 36. By applying further pressure on the retaining element 24, for instance the state illustrated in FIGS. 4 and 5 may be achieved. Thereafter, the mounting tool 12 may be detached from the fixation unit 20.

A comparison of FIGS. 12 and 13 shows that it is possible in certain embodiments to arrange the drivers 108 to be retractable and/or deflectable. In this way, the first shaft component 100 may pass the retaining element 24 when the mounting tool 12 is detached. In accordance with an alternative embodiment, the retaining element 24 may comprise a radial extension and/or a radial circumference that is at least sectionally smaller than the radial extension and/or the circumference of the anchor element 22 in the region of the counter surface 56. In this way, the first shaft component 100 may pass the retaining element 24 simply, and may act on the anchor element 22 without the need of deflectable drivers 108 and suchlike.

FIG. 14 illustrates an alternative embodiment of a mounting tool 12 that is exemplarily arranged for mounting the embodiment of the fixation unit 20 illustrated with reference to FIGS. 6 to 9.

As with the mounting tool 12 elucidated with reference to FIGS. 13 and 14, a shaft assembly 14 having a first shaft component 100 and a second shaft component 102 is provided. The first shaft component 100 is associated with the anchor element 22. The second shaft component 102 is associated with the retaining element 24.

The shaft assembly 14 is further provided with a pull unit 128 having the task of disengaging and removing the guide pin 78 when the retaining element 24 is locked with the anchor element 22 as desired.

The pull unit 128 comprises a clamping section 130. The pull unit 128 is arranged within the second shaft component 102, for instance, wherein the second shaft component 102 is, in turn, arranged within the first shaft component 100. The clamping section 130 may for instance involve clamping jaws or similar elements that cooperate with the guide pin 48 to detach and remove the guide pin 78 from the anchor element 22. A pull-off direction or detachment direction is indicated in FIG. 14 by 132.

With particular reference to FIG. 15 an inspection tool designated by 136 will be elucidated which may be also associated with the handling device 10.

The purpose of the inspection tool 136 is a disengagement and/or removal of the retaining element 24 from the assembly with the anchor element 22. As a locked assembly and/or a snap connection is formed during the assembly of the retaining element 24 with the anchor element 22, it is potentially beneficial to provide a specifically shaped inspection tool 136, at least in certain embodiments.

Structurally seen, the inspection tool 136 may be basically arranged similar to the mounting tool 12 illustrated in FIG. 11. Hence, for instance, a handpiece and a corresponding shaft assembly may be formed.

The inspection tool 136 comprises a downholder 138 that is provided with a pressure piece 140. The downholder 139 is arranged to act on the anchor element 22 so that sufficiently large disengagement forces and/or pull-off forces may be applied to the retaining element 24. By way of example, the pressure piece 140 is arranged to act on the connecting spike 60, for instance at the tip 62 thereof. In FIG. 15, an arrow designated by 142 elucidates a retaining direction and/or the direction of an applied retaining force.

The inspection tool 136 further comprises an actuator unit designated by 148. The actuator unit 148 comprises at least one pull-off hook or gripper 150. The gripper 150 is arranged to engage the retaining element 24 in a force-fit and/or positive-fit fashion. A respective operating direction is indicated in FIG. 15 by 154. In other words, in certain embodiments, the gripper 150 may engage the retaining element 24 laterally (radially) and/or laterally reach under the retaining element 24. In this way, pull forces may be applied to the retaining element 24 to disengage the retaining element 24 from the assembly with the anchor element 22, refer to a pull direction indicated by 156 in FIG. 15. Overall, the inspection tool 136 may be arranged similar to a pulling-off device.

It is however also conceivable to arrange the inspection tool 136 in such a way that the actuator unit 148 and/or the gripper 150 are arranged to at least sectionally destroy the retaining element 24. To this end, similar to a nut splitter, an impact may be applied to a circumferential section of the retaining element 24 to disengage the joined of the retaining element 24 with the anchor element 22. It goes without saying that also in this case the inspection tool 136 is arranged to remove the retaining element 24 without any residue.

When the retaining element 24 is removed, necessary manipulations at the tissue section 36 may be performed. Eventually, it is possible to feed a new retaining element 24, and to attach the retaining element 24 at the anchor element 22 by means of the mounting tool 12, refer particularly to FIG. 13.

For the handling of the fixation unit 20, a set of tools involving a mounting tool 12 and an inspection tool 136 for the disengagement of the retaining element 24 may be provided.

The present disclosure further relates to a method of fixing a tissue section at a bone that makes use of the fixation unit 20 as disclosed herein. The present disclosure further relates to a method of fixing a tissue section at a bone that makes use of the handling device 10 for the fixation unit 20 as disclosed herein.

What is claimed is:

1. A fixation unit for a suture-less fixation of tissue at a bone, wherein the fixation unit comprises:
   an anchor element that is arranged to be fixed to a bone,
   a retaining element that is arranged to be coupled with the anchor element to attach a tissue section, and
   a connecting spike that extends between a base body of the retaining element and a shaft body of the anchor element,
   wherein at least one of the anchor element and the retaining element is provided with a plurality of locking elements, such that the anchor element and the retaining element are lockable to one another via the plurality of locking elements and, in a locked state, a retaining zone for the tissue section is formed between the anchor element and the retaining element,
   wherein the anchor element and the retaining element form a snap-lock connection via the plurality of locking elements that enables, in a first direction, an approaching between the retaining element and the anchor element and that counteracts, in the locked state, a detachment movement in a second direction that is opposite to the first direction between the retaining element and the anchor element,
   wherein the plurality of locking elements are each arranged at differing positions along a longitudinal axis of the fixation unit, such that an interlock position between the anchor element and the retaining element is selectable when coupling the retaining element to the anchor element to allow for differing thicknesses of the retaining zone formed between the retaining element and the anchor element,
   wherein the connecting spike is arranged to extend through the tissue section when the retaining element and the anchor element approach one another, and
   wherein the connecting spike is formed at the retaining element, wherein at the anchor element a locking recess is formed, and wherein, in the locked state, the connecting spike at least sectionally extends therethrough.

2. The fixation unit as claimed in claim 1, wherein the retaining element is button shaped or plate shaped and provided with a contact surface facing the anchor element, wherein the retaining element and the anchor element engage one another in the locked state, and wherein the contact surface is arranged to bias the tissue section towards the anchor element.

3. The fixation unit as claimed in claim 2, wherein the contact surface of the retaining element is at least sectionally provided with elevations.

4. The fixation unit as claimed in claim 2, wherein the anchor element comprises a counter surface that is facing the contact surface, and wherein the counter surface and the contact surface define therebetween, in the locked state, the retaining zone for the tissue section.

5. The fixation unit as claimed in claim 3, wherein the anchor element comprises a counter surface that faces the contact surface and wherein the counter surface is at least sectionally provided with elevations that are adapted to the elevations of the contact surface of the retaining element to form therebetween, in the locked state, a labyrinth or a pattern of the elevations of the contact surface and the elevations of the counter surface.

6. The fixation unit as claimed in claim 1, wherein the connecting spike is provided with the plurality of locking elements that are arranged as a fluting or a circumferential notching that secures the position of the connecting spike in the locked state of the retaining element and the anchor element.

7. The fixation unit as claimed in claim 1, wherein the connecting spike, in the locked state, engages a locking recess that comprises the plurality of locking elements that are formed to be direction dependent, and that define a blocking direction.

8. The fixation unit as claimed in claim 1, wherein at the anchor element, a guide pin is arranged that is configured as a mounting aid, and that extends towards the retaining element, and wherein the connecting spike comprises a guide recess into which the guide pin is insertable to feed the connecting spike into the locking recess in the anchor element.

9. The fixation unit as claimed in claim 1, wherein adjacent locking elements of the plurality of locking elements are spaced apart from one another in an axial direction along the longitudinal axis of the fixation unit.

10. A handling device for inserting a fixation unit, comprising the following:
   a mounting tool, and
   a fixation unit comprising an anchor element that is arranged to be fixed to a bone, and a retaining element that is arranged to be coupled with the anchor element to attach a tissue section at the bone,
   wherein the anchor element and the retaining element are lockable to one another and form therebetween in a locked state a retaining zone for the tissue section,
   wherein the mounting tool comprises a shaft assembly having a distal support section at which the fixation unit is mountable,
   wherein the shaft assembly comprises a first shaft component for taking up the anchor element, and a second shaft component for taking up the retaining element,
   wherein the anchor element and the retaining element are jointly mountable by the mounting tool in a state axially displaced and disengaged from one another,
   wherein the first shaft component is arranged to feed the anchor element to the bone, and wherein the second shaft component is arranged to lock the retaining element and the anchor element with one another when the anchor element is fixed.

11. The handling device as claimed in claim 10,
wherein the first shaft component is arranged to transmit at least one of a feed force or a torque to the anchor element, and
wherein the second shaft component is arranged to be displaced relative to the first shaft component to move the retaining element towards the anchor element.

12. The handling device as claimed in claim 11, further comprising a pull unit that is arranged to detach a guide pin that is arranged at the anchor element from the anchor element when the retaining element is coupled with the anchor element, wherein the pull unit is provided at the shaft assembly.

13. The handling device as claimed in claim 10, further comprising an inspection tool for detaching the retaining element from the anchor element.

\* \* \* \* \*